United States Patent [19]

Taniguchi et al.

[11] Patent Number: 5,257,529
[45] Date of Patent: Nov. 2, 1993

[54] METHOD AND DEVICE FOR MEASUREMENT OF VISCOSITY OF LIQUIDS

[75] Inventors: Koichi Taniguchi, Funabashi; Kohei Ogawa, Tokyo, both of Japan

[73] Assignee: Nissho Corporation, Osaka, Japan

[21] Appl. No.: 28,615

[22] Filed: Mar. 8, 1993

Related U.S. Application Data

[63] Continuation of Ser. No. 813,937, Dec. 27, 1991, abandoned.

[30] Foreign Application Priority Data

Dec. 28, 1990 [JP] Japan .................. 2-418855

[51] Int. Cl.$^5$ ............................................. G01N 11/04
[52] U.S. Cl. ................... 73/54.09; 73/54.14; 73/54.04
[58] Field of Search ............... 73/54.01, 54.04, 54.06, 73/54.07, 54.09, 54.14

[56] References Cited

U.S. PATENT DOCUMENTS

| | | | |
|---|---|---|---|
| 3,048,999 | 8/1962 | Pochan | 73/54 |
| 3,136,440 | 6/1964 | Krug et al. | 128/764 |
| 3,586,064 | 6/1971 | Brown et al. | 73/864.74 |
| 3,720,097 | 3/1973 | Kron | 73/55 |
| 3,782,173 | 1/1974 | Van Vessem et al. | 73/56 |
| 3,901,402 | 8/1975 | Ayres | 128/764 |
| 3,920,557 | 11/1975 | Ayres | 128/764 |
| 4,083,363 | 4/1978 | Philpot, Jr. | 73/55 |
| 4,492,634 | 1/1985 | Villa-Real | 128/763 |
| 4,517,830 | 5/1985 | Gunn et al. | 73/54 |
| 4,750,351 | 6/1988 | Ball | 73/54 |
| 4,858,127 | 8/1989 | Kron et al. | 73/55 |

FOREIGN PATENT DOCUMENTS 0337821 10/1989 European Pat. Off. .

OTHER PUBLICATIONS

"A Simple Capillary Viscometer" Physics Education vol. 10, No. 2, Mar. 1975, C. Bowlt.

*Primary Examiner*—Hezron E. Williams
*Assistant Examiner*—George M. Dombroske

[57] ABSTRACT

A viscosity of liquids is measured by inserting one end of a fine tube into one end of a tubular vessel sealed and maintained at a reduced pressure, while dipping the other end of the fine tube in a liquid to be measured, to cause the liquid to flow into the the vessel through the fine tube under the influence of a difference in pressure between both ends of the fine tube, detecting an internal pressure of the tubular vessel with a pressure sensor connected to the vessel to measure a change of an internal pressure of the vessel with passage of time and a change of a flow rate of the liquid passing through the fine tube with passage of time, and determining a viscosity of the liquid from the change of the internal pressure of the vessel and the change of the flow rate of the liquid. The pressure sensor is connected to the vessel by a device for piercing the other stopper and its output signals are fed to a computer through an A/D converter to calculate the viscosity of the liquid.

9 Claims, 10 Drawing Sheets

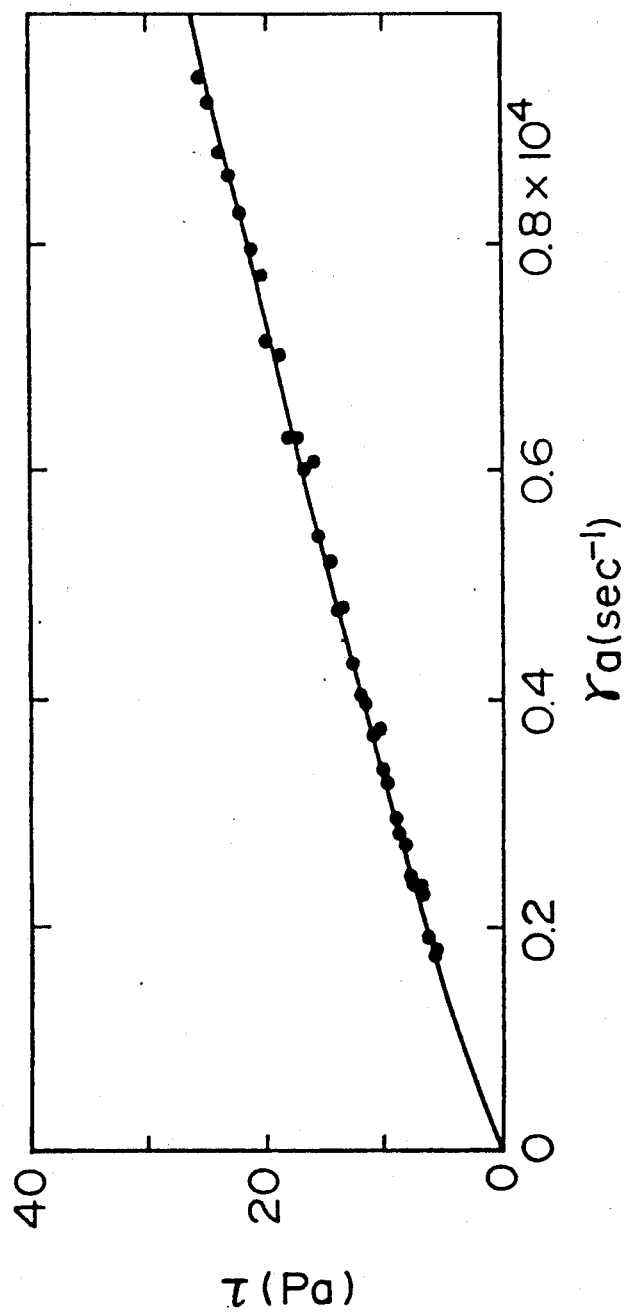

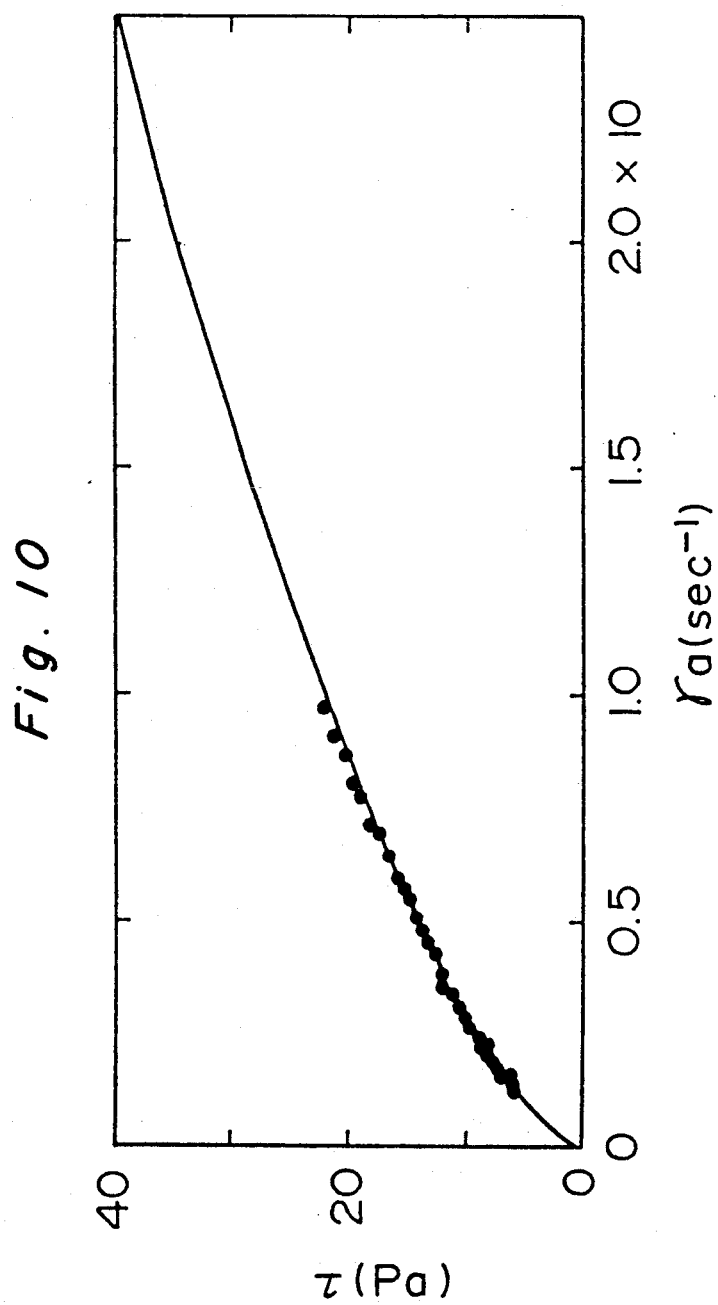

METHOD AND DEVICE FOR MEASUREMENT OF VISCOSITY OF LIQUIDS

This application is a continuation of application Ser. No. 07/813,937, filed on Dec. 27, 1991, now abandoned.

BACKGROUND OF THE INVENTION

1. Field of the Invention

The present invention relates to a method and device for measurement of a viscosity of liquids and, more particularly, a method and device applicable to measurement of the viscosity of bloods.

2. Description of Related Art

It is well-known that the health conditions of a person influence the viscosity of bloods. In fact, the viscosity of a blood of a person who suffers from anemia, chronic renal insufficiency requiring hemodialysis, myocardial infarction, diabetes mellitus or malignant tumor, differs greatly from that of a person in normal health. In advanced nations, with an increase in the average age of the population, adult diseases such as, for example, myocardial infarction, thrombo-embolism and diabetes mellitus are gradually increasing. Thus, the measurement of the viscosity of bloods is an important and effective factor essential for therapy and/or prevention of diseases.

As is known, the blood is non-Newtonian in its flow characteristics, whereas the blood plasma behaves Newtonian. It is said, therefore, that the non-Newtonian behaviors of the blood result from the presence of blood corpuscles suspended in the blood plasma. In particular, it is said that factors which influence the flow characteristics of the blood are the orientation of blood corpuscles and their various shapes including disc shapes with concave surfaces, streamlined shapes or projectile shapes. The effect of such factors on the flow characteristics varies with a period of time elapsed from the blood collecting, and is affected by addition of other substances such as, for example, anticoagulants to the blood. Thus, the best way to determine the flow characteristics of blood including its non-Newtonian behaviors is to choose the blood running in the body as the object of the measurement.

However, there is no viscometry which makes it possible to directly measure the flow characteristics of the blood running in the body. To this end, it is inevitable to use collected blood as the object of measurement. It is therefore required to measure the flow characteristics of the blood correctly in the least time possible after blood-collecting, as well as to collect the blood without incorporating any other materials such as anticoagulants into the blood.

In addition, in order to adapt rheological blood tests to a routine clinical medicine, it is required to satisfy the following three conditions: (a) the measurement can be made with the natural blood; (b) the measurement can be made instantly at the bed side; and (c) the viscometer is easy to operate and operable for any person.

So far, various devices have been developed to measure the viscosity of liquids or solutions. In the sphere of clinical medicine, however, there have been employed two devices, i.e., a capillary viscometer and a rotation viscometer. In the former, the viscosity of a liquid is measured by introducing the liquid into the capillary viscometer, and then causing the liquid to flow under external forces such as the gravitational force through a capillary or a fine tube of uniform bore to obtain the time required for its meniscus to pass through between predetermined levels. The measurement is carried out several times at various flow rates and under pressure heads resulting from a length of the capillary. Such a capillary viscometer has been used widely to measure the viscosity of blood plasma. However, it is rarely the case that the capillary viscometers are applied to measure the viscosity of blood as the natural blood is non-Newtonian in its flow characteristics.

The measurement of the viscosity of bloods has generally been carried out with rotation viscometers. A typical rotation viscometer comprises two concentric cylinders, the inner or outer cylinder being rotated in or rotated around the fixed outer or inner cylinder. In such a viscometer, the liquid is placed between two cylinders and either of the cylinders is rotated around its axis to measure its torque.

However, the rotation viscometers have the following disadvantages: (a) several measurements must be made on the same blood at different shear stresses; (b) calculations are troublesome and lead to noticeable errors as they require graphical differentiation of logarithmic values; (c) special and unstable flows such as Taylor vortex takes place at high rotating rates; (d) the liquid to be examined generates heat by its viscosity; (e) there is a fear of causing deflection of blood corpuscles by means of the centrifugal force; (f) the measurement for each specimen takes a long time; and (g) the viscometer is troublesome to handle as the viscometer must be cleaned after every measurement by washing it with water and then drying the same to remove the blood adhered thereto.

To solve these problems, various new methods employing a roller pump system or a hollow fiber module have been proposed to measure the viscosity of bloods. However, none of the viscometers of the prior art satisfies all the conditions required for application to the clinical medicine.

SUMMARY OF THE INVENTION

It is therefore an object of the present invention to provide a method for measurement of viscosities of liquids, which makes it possible to achieve correct and rapid measurement of the viscosity of a liquid with ease, using a small amount of the liquid.

Another object of the present invention is to provide a device for measurement of viscosity of liquids or a viscometer, which is compact in structure, easy to operate and transport, and low in manufacturing cost.

These and other objects of the present invention are achieved by providing a method for measurement of a viscosity of liquids, comprising the steps of (a) inserting one end of a fine tube of uniform bore into one end of a tubular vessel sealed and maintained at a reduced pressure, while dipping the other end of said fine tube in a liquid to be measured, to cause the liquid to flow into said vessel through the fine tube under the influence of a difference in pressure between both ends of said fine tube, (b) detecting an internal pressure of said tubular vessel with a pressure sensor connected to the other end of the vessel to determine each flow rate of the liquid passing through said fine tube with passage of time, as well as to determine each change rate of an internal pressure of said vessel with passage of time, (c) determining a viscosity of the liquid from the resultant flow rates of the liquid and the resultant change rate of the internal pressure.

The above method can be carried out with a device for measurement of a viscosity of liquids, which comprises a tubular vessel sealed and maintained at a reduced pressure by a pair of rubber-like stoppers fitted in each opening of said vessel, a hollow fine tube of uniform bore adapted to be pierced through one of said stoppers to let it enter said vessel, a pressure sensor adapted to be connected to said vessel by a means for piercing the other stopper to detect an internal pressure of said vessel, an A/D converter electrically connected said pressure sensor to convert output signals of the sensor to digital signals, and a computer for processing output signals of said A/D converter to determine a shear stress and a shear rate of the liquid, as well as to determine the viscosity of the liquid from the resultant shear stress and shear rate by the following equations:

$$\gamma(\tau_w) = -du/dr = 3\gamma_a/4 + (\tau_w/4)(d\gamma_a/d\tau_w) \qquad (10)$$

$$\tau_w = \Delta PR/(2L) \qquad (8)$$

$$\gamma_a = 4Q/(\pi R^3) \qquad (9)$$

where $\gamma(\tau_w)$ is a shear rate, or velocity gradient, of the liquid, $\tau_w$ is a shear stress of the liquid, $\Delta P$ is a pressure difference between both ends of the fine tube, R is a radius of the fine tube, L is a length of the fine tube, Q is a flow rate of the liquid per unit time, and $\gamma_a$ is the apparent velocity gradient at a point on the wall.

These and other objects and features of the present invention will become apparent from the following description with reference to the accompanying drawings, which show, by way of example only, one preferred embodiment thereof.

BRIEF EXPLANATION OF THE DRAWINGS

FIG. 5 is a graph showing the relationship between the shear stress and the shear rate of the blood;

FIG. 10 is a graph showing the relationship between the shear stress and the shear rate of an aqueous solution of polyacryl amide.

DETAILED EXPLANATION OF THE PREFERRED EMBODIMENT

Figure 1:
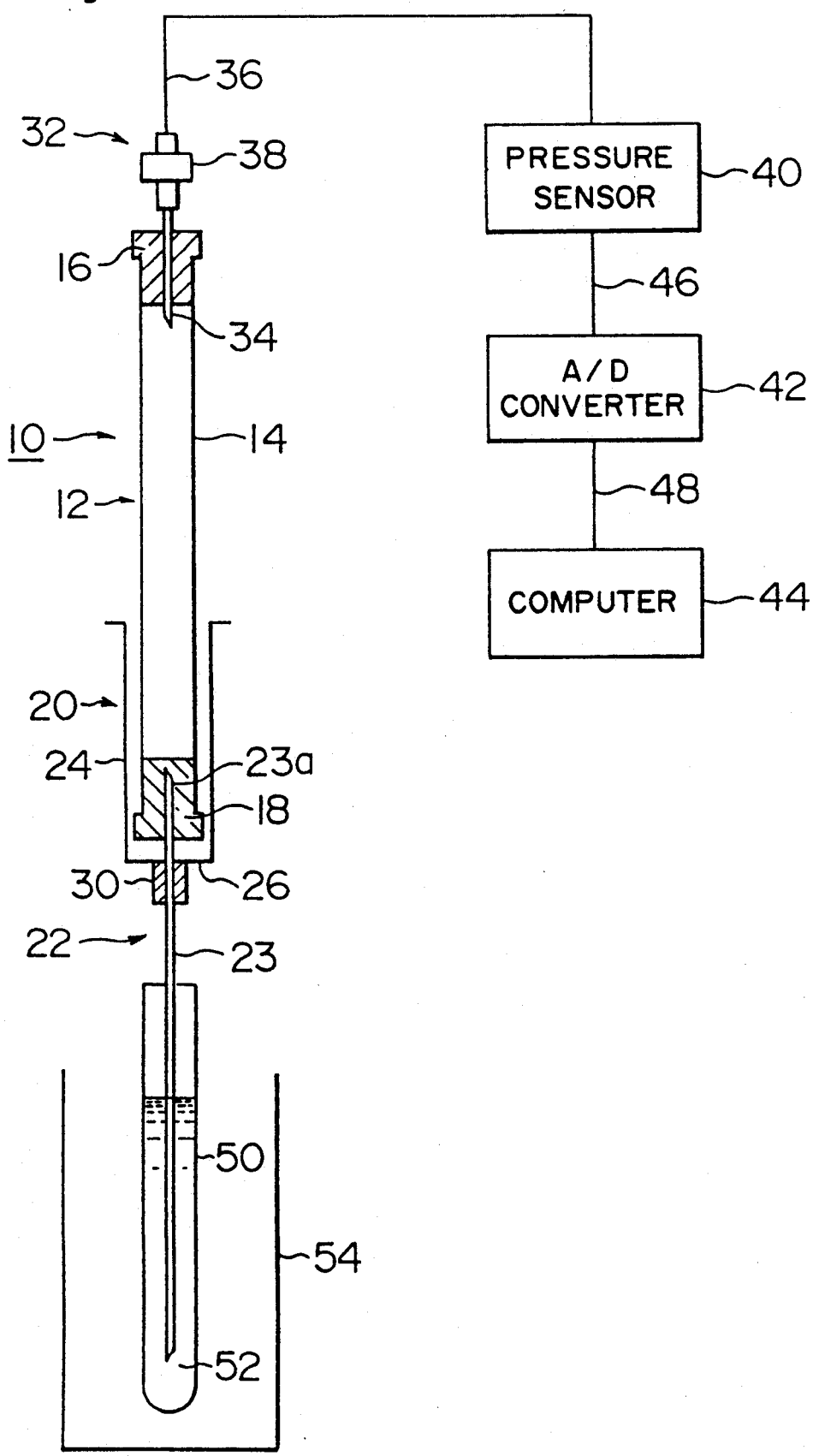
FIG. 1 is a schematic diagram of a device for measurement of viscosity of liquids embodying the present invention.

Referring now to FIG. 1, there is shown a schematic diagram of a device for measurement of viscosity of liquids, i.e., a viscometer, 10, embodying the present invention. The device 10 includes a tubular vessel 12, a suction tube assembly 20, a liquid container 50, a pressure sensor 40, an A/D converter 42 electrically connected to the sensor 40, and a computer 44 electrically connected to the A/D converter 42.

The tubular vessel 12 includes a tubular body 14 of uniform bore with open ends. This tubular body 14 is made of glass or a plastic material. The tubular body 14 is previously evacuated to a given pressure, and hermetically sealed by a pair of rubber-like stoppers 16 and 18 fitted in the openings of the tubular body 14 to maintain its reduced pressure. In this embodiment, the vessel is evacuated to a reduced pressure, for example, a pressure which is lower than the atmospheric pressure by 180 mmHg. The stoppers 16, 18 are made of an elastic material, preferably, butyl rubber. The stopper may be tapered or provided at one end thereof with a flange to prevent it from falling into the tubular body 14 by the difference in pressure between the internal pressure of the vessel and the atmosphere.

The suction tube assembly 20 includes a hollow piercing needle 22, which has a sharp piercing tip 23a at one end of a cannula 23 and a hub 30 arranged close to the tip 23a, and a vessel holder 24 concentrically arranged on the piercing needle 22. The cannula 23 is composed of a fine tube of uniform bore, made of a metal. Preferred materials for the cannula 23 are stainless steels such as, for example, SUS 304 defined by JIS.

The vessel holder 24 includes a short tubular member closed at one end and is so designed that it has a length shorter than that of the tubular body 14, and an inner diameter greater than the outer diameter of the tubular body 14 to allow the latter to be moved smoothly. The piercing needle 22 is provided with a male screw on a surface of the hub 30, so that it engages with a female screw provided in the center of the bottom 26 of the holder 24 to prevent axial movement of the needle with respect to the holder 24. The position of the hub 30 is so determined that the piercing tip 23a of the needle 22 can extend into the interior of the vessel 12 when the needle 22 is inserted into the elastic stopper 18 until the bottom 26 of the holder 24 comes into contact with the bottom of the stopper 18.

The liquid container 50 is charged with a liquid to be examined, and placed in a thermostat 54 to keep its temperature constant. Any container may be used, but it is preferred to use a commercially available test tube. Also, any thermostat may be used, but it is preferred to use a thermostat so designed that several containers 50 can be charged therein at a time, to improve efficiency of examination.

The pressure sensor 40 is connected to the tubular vessel 12 by means of a connecting device 32 to detect a pressure in the vessel 12. The connecting device 32 includes a hollow piercing needle 34 with a hub 38, and a connecting tube 36 made of a metal. The connecting tube 36 is generally made of a metal such as a stainless steel, and is hermetically connected at one end to the hub 38 and at the other end to the pressure sensor 40 to correctly transfer the internal pressure of the vessel 12 to the sensor 40.

The pressure sensor 40 is electrically connected to the A/D converter 42 by lead wires 46, which is in turn connected to the computer 44 by lead wires 48. The sensor 40 detects the internal pressure of the vessel 12 and converts it to an electrical signal corresponding to that pressure. The signal from the sensor is fed to the A/D converter 40 where the analog signal is converted to digital signals. The digital signals are fed to the computer 44 to determine the viscosity of the liquid to be examined. The computer 44 executes a viscosity measuring program stored in its memories (ROM), as mentioned below. Any commercial computers may be used for this purpose.

The flow rate of the liquid running through the fine tube varies with the viscosity of the liquid and the change rate of the internal pressure of the tubular vessel 12 for a given period of time depends on the flow rate of the liquid. To this end, the internal pressure of the vessel 12 is detected by the pressure sensor 40 at given intervals and transferred through the A/D converter 42 to the computer 44 where the viscosity of the liquid is determined.

It is essential for the piercing needle 22 to have a sharp tip at one end thereof for piercing the elastic stopper 18, but there is no need to provide a sharp cut tip on both ends of the cannula 23.

In the above embodiment, the piercing needle 22 is composed of an elongated hollow metal tube, or an elongated cannula with a small radius, but this piercing needle may take any desired structure. For example, the piercing needle 22 may be constituted by into two parts, i.e., a fine tube of a metal with a sharp end, and a fine tube of a plastic material, connected to each other by a joint.

Using the device of the above construction, the method for measurement of a viscosity of liquids according to the present invention is carried out in the following manner.

Figure 2:
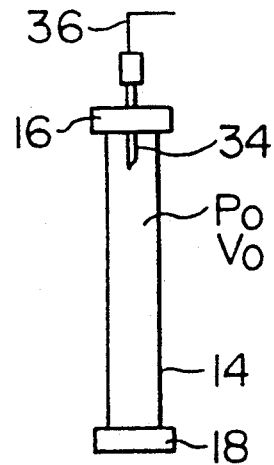
FIG. 2 is a section view of a tubular vessel employed in the device of FIG. 1, with a connecting needle being attached thereto.

The vessel holder 24 is held vertically by a suitable holder (not shown) and the piercing needle 34 of the connecting device 32 is pierced into the elastic stopper 16 until its lower end extends into the interior of the vessel 12, as shown in FIG. 2.

After or before the above operation, the container 50 containing a liquid to be measured, 52, is placed in the thermostat 54 maintained at a test temperature, and allowed to stand for a certain period of time sufficient to reach the test temperature. Then, the free end or lower end of the piercing needle 22 is dipped into the liquid 52 in the container 50.

Figure 4A:
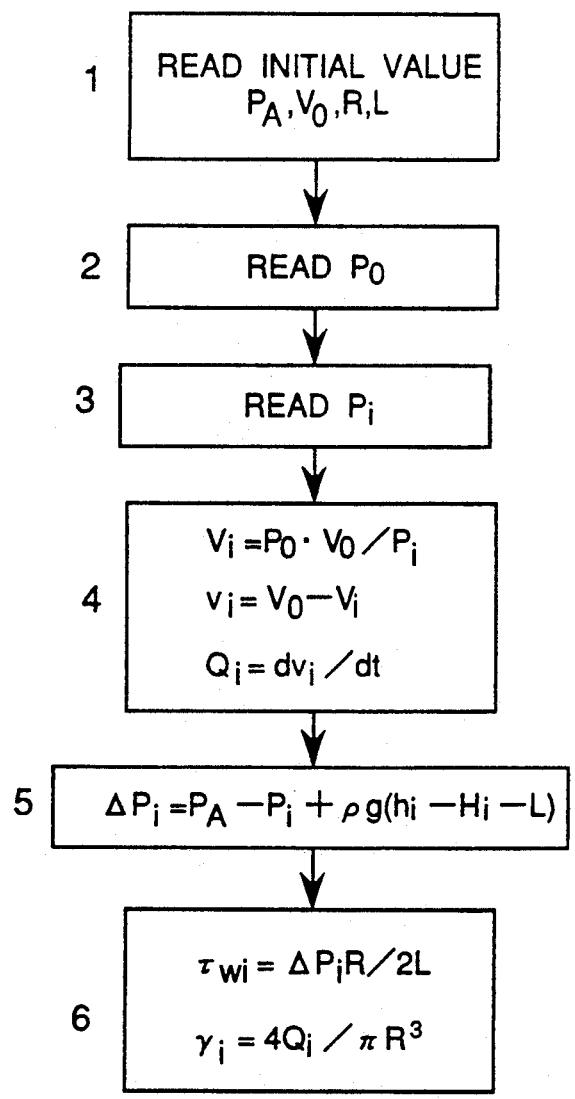
FIGS. 4A and 4B are flow charts showing the sequence of operation of a computer used in the device of FIG. 1 to calculate the viscosity of liquid.
Figure 4B:
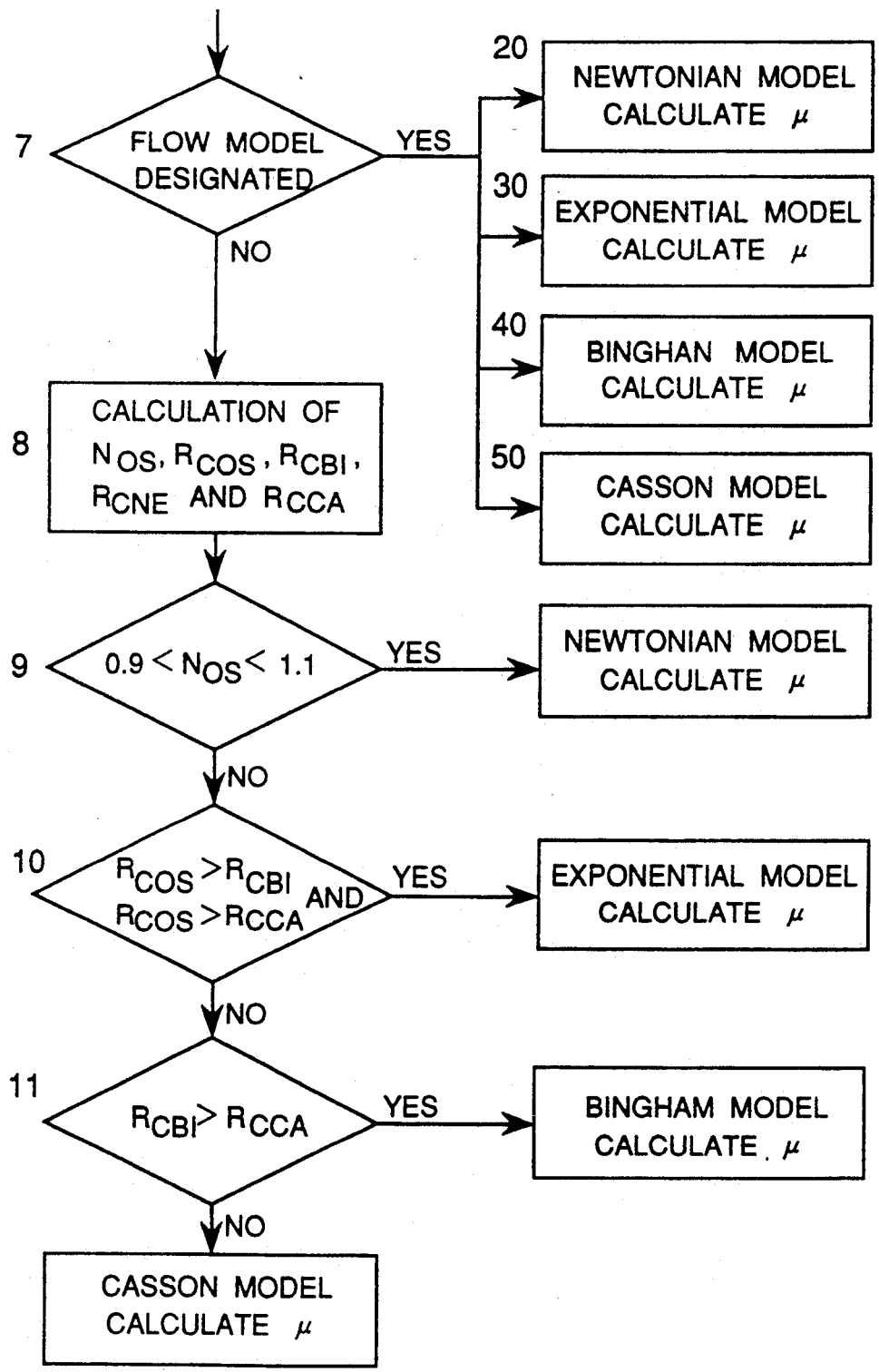

On the other hand, the computer 44 is turned on and receives the atmospheric pressure, $P_A$, the initial volume of the vessel $V_0$, the radius of the fine tube or capillary, R, and the length of the piercing needle 22, L, through a key board (not shown) at step 1 in FIG. 4. The initial internal pressure of the vessel, $P_0$, is measured via the sensor 40 and A/D converter 42, at step 2.

Figure 3:
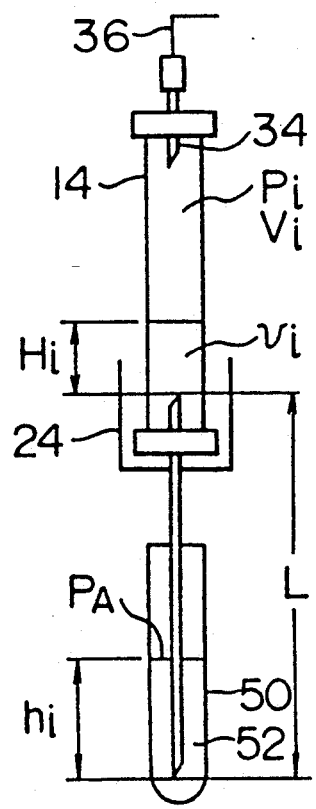
FIG. 3 is a section view of an essential part of the device of FIG. 1, illustrating the tubular member being charged with a liquid to be measured.

Then, the piercing tip 23a of the cannula 23 is pierced into the stopper 18. In FIGS. 1 or 2, the piercing needle 22 is illustrated as being terminated in the stopper 18, but the cannula 23 is further pierced into the elastic stopper 18 until its piercing tip 23a extends into the interior of the vessel 12 through the stopper 18, as shown in FIG. 3. As soon as the piercing tip 23a enters into the interior of the vessel 12, the liquid 52 in the container 50 begins to flow into the vessel 12 through the cannula 23 by the difference between the pressure acting on the meniscus of the liquid 52 (actually the atmospheric pressure) and the internal pressure of the tubular vessel 12.

With an increase in the amount of the liquid 52 charged into the vessel 12, as illustrated in FIG. 3, the volume of the uncharged space of the vessel 12 reduces, while the internal pressure of the vessel 12 increases. The inflow of the liquid continues until the internal pressure of the vessel 12 becomes equal to the hydrostatic pressure at the lower end of the fine tube, which can be regarded to be identical with the atmospheric pressure, $P_A$.

During the above period, the internal pressure, $P_i$, of the vessel 12 is measured and converted into electrical signals by the pressure sensor 40. The output signals are fed to the A/D converter 42 where the signals from the sensor 40 are converted to digital signals.

The digital signals from the A/D converter 42 are supplied to the computer 44 via I/O ports (not shown) of the latter at a certain interval of time, $\Delta t$, whereby calculations are carried out at step 4 to determine the charged amount of the liquid in the vessel at time $t_i$, $v_i$, the volume of the uncharged space of the vessel at time $t_i$, $V_i$, and the flow rate of the liquid, $Q_i$.

Then, the program proceeds to step 5 where the pressure difference, $\Delta P_i$, between both ends of the fine tube at time $t_i$ is calculated. The calculated values of $Q_i$ are stored in memories (RAM) of the computer along with the values of pressure difference $\Delta P_i$. The pressure change may be converted to the volume change of the uncharged space of the vessel 12 on the basis of Boyle's law.

Then, the program proceeds to step 6 where the shear stress, $\tau_i$, and the apparent shear rate, $\gamma_{ai}$, are respectively calculated from the flow rate of the liquid, $Q_i$, and the pressure difference, $\Delta P_i$.

The equations required in calculation are derived from the following theoretical considerations. Assuming that the product of the pressure in the vessel and the volume of unchanged space of the vessel is constant, a pressure $V_i$ in the uncharged space of the vessel at time $t_i$ is given by equation 1, $$P_0 V_0 = P_i V_i \tag{1}$$

where $P_0$ is the initial pressure at time $t_0$, $V_0$ the initial volume at time $t_0$, and $P_i$ the pressure at time $t_i$.

Since the volume, $v_i$, of the liquid in the vessel at time $t_i$ is obtained by equation 2, the flow rate of the liquid, $Q_i$, at time $t_i$ is given by equation 3:

$$v_i = V_0 - V_i \tag{2}$$

$$Q_i = dv_i/dt \tag{3}$$

On the other hand, the pressure difference, $\Delta P_i$, between ends of the fine tube at time $t_i$ is given by equation 4, $$\Delta P_i = (P_A + \pi g h_i) - (P_i + \pi g H_i) - \pi g L \tag{4}$$

where $\pi$ is the density of the liquid, g is the acceleration of gravity, $P_A$ is the atmospheric pressure, $P_i$ is the pressure acting on the meniscus of liquid in the vessel at time $t_i$, $h_i$ is the length of the needle 22 being immersed in the liquid at time $t_i$, $H_i$ is the distance between the end of the needle 22 and the meniscus of the liquid 52 in the vessel 12 at time $t_i$, and L is the length of the needle, as illustrated in FIG. 3. The values of $h_i$ and $H_i$ can be obtained in the process of calculation of $Q_i$, provided that the vessel 14 and container 50 are of a uniform bore and that the thickness of the piercing needle 23 can be neglected.

Since the fine tube 23 and the vessel 14 are of uniform bore, $h_i$ and $H_i$ in the above equation are respectively obtained during the course of determination of the value of $Q_i$, i.e., by diving the charged amount of the liquid with the cross-sectional area of the fine tube 23 or vessel 14.

By using the fine tube of which the length is not less than 260 times the inner diameter of the fine tube, the end effects in charge or discharge on the pressure difference of the fine tube can be minimized to less than 5%.

Rearrangement of equation 4 provides $$\Delta P_i = P_A - P_i + \pi g(h_i - H_i - L) \tag{5}$$

The shear stress, $\tau_{wi}$, and the apparent shear rate, $\gamma_{ai}$, at time $t_i$, are given by the following equations.

$$\tau_{wi} = \Delta P_i R/(2L) \tag{6}$$

$$\gamma_{ai} = 4Q_i/(\pi R^3) \tag{7}$$

In practice, the pressure difference, $\Delta P_i$, is obtained as the average value of two measurements detected at an interval of time, $\Delta t$, so that the flow rate of the liquid, $Q_i$, is obtained as the average value by $$Q_i = (v_i - v_{i-1})/\Delta t \tag{3'}$$

Thus, the shear stress and the shear rate are obtained as the average values by the following equations, $$\tau_w = \Delta P R/(2L) \tag{8}$$

$$\gamma_a = 4Q/(\pi R^3) \tag{9}$$

where $\gamma_a$ is the apparent shear rate or apparent velocity gradient, and R is the radius of the fine tube.

The general velocity gradient is a function of the shear stress, $\gamma(\tau_w)$, and is given by equation 10, $$\gamma(\tau_w) = -du/dr = 3\gamma_a/4 + (\tau_w/4)(d\gamma_a/d\tau_w) \tag{10}$$

On the other hand, the viscosity of the liquid flowing in the steady state is defined as the ratio of shear stress to the apparent shear rate at a point on the wall, and given by the following equations corresponding to the flow model of the liquid.

If the liquid is a Newtonian fluid, the apparent shear rate is related to the shear stress by equation 11, $$\gamma_a = \alpha \tau_w \tag{11}$$

where $\alpha$ is constant.

If the liquid is a exponential fluid, the apparent shear rate is related to the shear stress by equation 12, $$\gamma_a = (\alpha \tau_w)^{1/n} \tag{12}$$

where n is power law exponent.

If the liquid is a Bingham fluid, the apparent shear rate is related to the shear stress by equation 13, $$\gamma_a = \alpha(\tau_w - \tau_{BI}) \tag{13}$$

where $\tau_{BI}$ is given from the yield stress by the following equation:

$$\tau_r = (3/4)\tau_{BI}$$

If the liquid is a Casson fluid, the apparent shear rate is related to the shear stress by equation 14, $$\gamma_a^{1/2} = \alpha(\tau_w^{1/2} - \tau_{CA}) \tag{14}$$

where $\tau_{CA}$ is Casson yield stress given from the yield stress, $\tau_r$, by the following equation:

$$\tau_r = (49/64)\tau_{CA}^2$$

Accordingly, the flow characteristics, $\gamma(\tau_w)$, and the coefficient of viscosity, $\mu$, are respectively given by equations 15 to 18, which are derived from the above equations 8 to 14.

(1) Newtonian model $$\mu = 1/\alpha = \tau_w/\gamma_a \tag{15}$$

$$\gamma(\tau_w) = \gamma_a$$

(2) Exponential model $$\mu = (4n/(\alpha(3n+1)))^n(\gamma_a)^{n-1} \tag{16}$$

where n is power law exponent.

$$\gamma(\tau_w) = \alpha((3n+1)/4n)\tau_w^{1/n}$$

(3) Bingham model $$\mu = 1/\alpha \tag{17}$$

$$\gamma(\tau_w) = \alpha(\tau_w - 3\beta/4)$$

where $\beta$ is given by equation: $\tau_{wi} = 3\beta/4$, (4) Casson model $$\mu = \alpha^2 \tag{18}$$

$$\gamma(\tau_w)^{1/2} = (\tau_w^{1/2} - \tau_{CA})/\alpha$$

where $\tau_{CA}$ is the Casson yield stress.

Thus, if the flow characteristics of the liquid are previously known to the operator, the equation to be used can be manually designated by means of a key board (not shown) of the computer.

After completing calculation of the shear stress, $\tau_i$, and the apparent shear rate, $\gamma_{ai}$, judgement is made at step 7 as to whether the flow model of the liquid is designated by the operator. If the flow model has been designated, the program proceeds to the designated step 20, 30, 40 or 50 where a coefficient of viscosity, $\mu$, is determined by one of equations 15 to 18 mentioned above.

However, if the flow model of the liquid to be examined is not known to the operator, it is impossible to designate the flow model of the liquid. To solve this problem, the device of the present invention further includes a means for determination of the flow characteristics of the liquid. This may be done automatically in the following manner.

If the flow model of the liquid is not designated, the program proceeds to step 8 where the structural viscosity index for the exponential flow model, $N_{os}$, a correlation coefficient for the Newtonian model, $R_{CNE}$, a correlation coefficient for the Bingham model, $R_{CBI}$, and a correlation coefficient for the Casson model, $R_{CCA}$, are calculated from the values of $\tau_{wi}$ and $\gamma_{ai}$ stored in the memory of the computer. The equations to be used in calculations are:

$$N_{OS} = \frac{\Sigma \left( \log \gamma_{ai} - \frac{\Sigma \log \gamma_{ai}}{CN} \right) \left( \log \tau_{wi} - \frac{\Sigma \log \tau_{wi}}{CN} \right)}{\Sigma \left( \log \gamma_{ai} - \frac{\Sigma \log \gamma_{ai}}{CN} \right)^2}$$

where CN is the number of data.

$$R_{CNE} = \frac{\Sigma \gamma_{ai} \cdot \tau_{wi}}{(\Sigma \gamma_{ai}^2 \cdot \Sigma \tau_{wi}^2)^{\frac{1}{2}}}$$

$$R_{COS} = \frac{\Sigma \left( \log \gamma_{ai} - \frac{\Sigma \log \gamma_{ai}}{CN} \right) \left( \log \tau_{wi} - \frac{\Sigma \log \tau_{wi}}{CN} \right)}{\left\{ \Sigma \left( \log \gamma_{ai} - \frac{\Sigma \log \gamma_{ai}}{CN} \right)^2 \cdot \Sigma \left( \log \tau_{wi} - \frac{\Sigma \log \tau_i}{CN} \right)^2 \right\}^{\frac{1}{2}}}$$

$$R_{CBI} = \frac{\Sigma \left( \gamma_{ai} - \frac{\Sigma \gamma_{ai}}{CN} \right) \left( \tau_{wi} - \frac{\Sigma \tau_{wi}}{CN} \right)}{\left\{ \Sigma \left( \gamma_{ai} - \frac{\Sigma \gamma_{ai}}{CN} \right)^2 \cdot \Sigma \left( \tau_{wi} - \frac{\Sigma \tau_{wi}}{CN} \right)^2 \right\}^{\frac{1}{2}}}$$

$$R_{CCA} = \frac{\Sigma \left( \gamma_{ai}^{\frac{1}{2}} - \frac{\Sigma \gamma_{ai}^{\frac{1}{2}}}{CN} \right) \left( \tau_{wi}^{\frac{1}{2}} - \frac{\Sigma \tau_{wi}^{\frac{1}{2}}}{CN} \right)}{\left\{ \Sigma \left( \gamma_{ai}^{\frac{1}{2}} - \frac{\Sigma \gamma_{ai}^{\frac{1}{2}}}{CN} \right)^2 \cdot \Sigma \left( \tau_{wi}^{\frac{1}{2}} - \frac{\Sigma \tau_{wi}^{\frac{1}{2}}}{CN} \right)^2 \right\}^{\frac{1}{2}}}$$

Then, the flow model of the liquid being examined is determined at steps 9 to 11 on the basis of the calculated values of these correlation coefficients. If the value of $N_{OS}$ is greater than 0.9 but smaller than 1.1, the liquid is judged at step 9 to be a Newtonian fluid. If the value of $N_{OS}$ is out of the above range, the programs proceeds to step 10 where judgement of the flow model is made on the basis of the values of $R_{COS}$, $R_{CBI}$ and $R_{CCA}$. If $R_{COS}$ is greater than $R_{CBI}$ and $R_{CCA}$, the liquid is judged to be an exponential liquid. If $R_{COS}$ is not greater than $R_{CBI}$ or $R_{CCA}$, the program proceeds to step 11 where the comparison is made as to whether the value of $R_{CBI}$ is greater than that of $R_{CCA}$. If the value of $R_{CBI}$ is greater than that of $R_{CCA}$, the liquid is judged to be a Bingham fluid. If the value of $R_{CBI}$ is not greater than that of $R_{CCA}$, the liquid is judged to be a Casson fluid.

After the flow model of the liquid is determined, the coefficient of viscosity of the liquid is calculated by the following equation.

(1) Newtonian model $$\mu = a = \frac{\Sigma \gamma_{ai} \cdot \tau_{wi}}{\Sigma \gamma_{ai}^2}$$

(2) Exponential model $$a = \exp \left( \frac{\Sigma \log \tau_{wi}}{CN} - \frac{N \cdot \Sigma \log \gamma_{ai}}{CN} \right)$$

$$\mu = a \left( \frac{4}{3n + 1} \right)^n \cdot 5000^{n-1}$$

(3) Bingham model $$\mu = a = \frac{\Sigma \left( \gamma_{ai} - \frac{\Sigma \gamma_{ai}}{CN} \right) \left( \tau_{wi} - \frac{\Sigma \tau_{wi}}{CN} \right)}{\Sigma \left( \gamma_{ai} - \frac{\Sigma \gamma_{ai}}{CN} \right)^2}$$

$$\tau_r = \frac{3}{4} \tau_{BI}$$

(4) Casson model $$a = \frac{\Sigma \left( \gamma_{ai}^{\frac{1}{2}} - \frac{\Sigma \gamma_{ai}^{\frac{1}{2}}}{CN} \right) \left( \tau_{wi}^{\frac{1}{2}} - \frac{\Sigma \tau_{wi}^{\frac{1}{2}}}{CN} \right)}{\Sigma \left( \gamma_{ai}^{\frac{1}{2}} - \frac{\Sigma \gamma_{ai}^{\frac{1}{2}}}{CN} \right)^2}$$

$$\mu = a^2$$

$$\tau_r = \frac{49}{64} \tau_{CA}^2$$

As can be seen from the above, the method according to the present invention is characterized by the fact that it comprises the steps of detecting the pressure difference which continuously varies with time, and continuously calculating the corresponding flow rate of the liquid to be examined on the basis of Boyle's Law from the detected pressure differences. Thus, there is no need to repeat the measurement on the same liquid. In contrast therewith, it is essential for the conventional method to make the measurements on the same liquid several times at various pressure differences between the capillary ends.

Also, the method of the present invention makes it possible to determine the viscosity of liquids with a small amount of the liquid, for example, 5 to 8 ml in the short time of 1 or 2 minutes, which in turn makes it possible to considerably improve efficiency of viscosity measurement. Further, the method of the present invention is effective for the measurement of the viscosity of bloods since it is preferred to complete the measurement in a few minutes after blood-collecting.

According to the present invention, data can be collected in detail as occasion demands, thus making it easy to achieve graphic differentiation with a high accuracy of better than 5%. It is possible with the present invention to measure the viscosity with high reproducibility in a wide range of the shear rate.

The present invention makes it possible to measure the viscosity of the blood without causing hemolysis as the time required for the blood to pass through the fine tube is considerably short as compared with the conventional methods. The present invention makes it possible to use the same blood for the measurements of other clinical purposes.

The device of the present invention is simple to operate, and very compact as compared with the conventional ones.

Since some parts of the device such as the vessel and fine tube, which are brought into in contact with the liquid, are disposable, there is no fear of infection even if the device is used to measure the viscosity of bloods contaminated by pathogenic bacteria such as hepatitis virus.

EXPERIMENT 1

Using the above device, the measurements of the viscosity of the human blood were carried out at 27° C. in the manner mentioned above. Results are shown in FIG. 5.

It has been said that the human blood is a Casson fluid. As can be seen from FIG. 5, it can be said that the human blood can be regarded as a Newtonian fluid, although it behaves non-Newtonian in the flow characteristics and may be regarded as a Bingham fluid or an exponential fluid when the shear rate is considerably small.

EXPERIMENT 2

Figure 6:
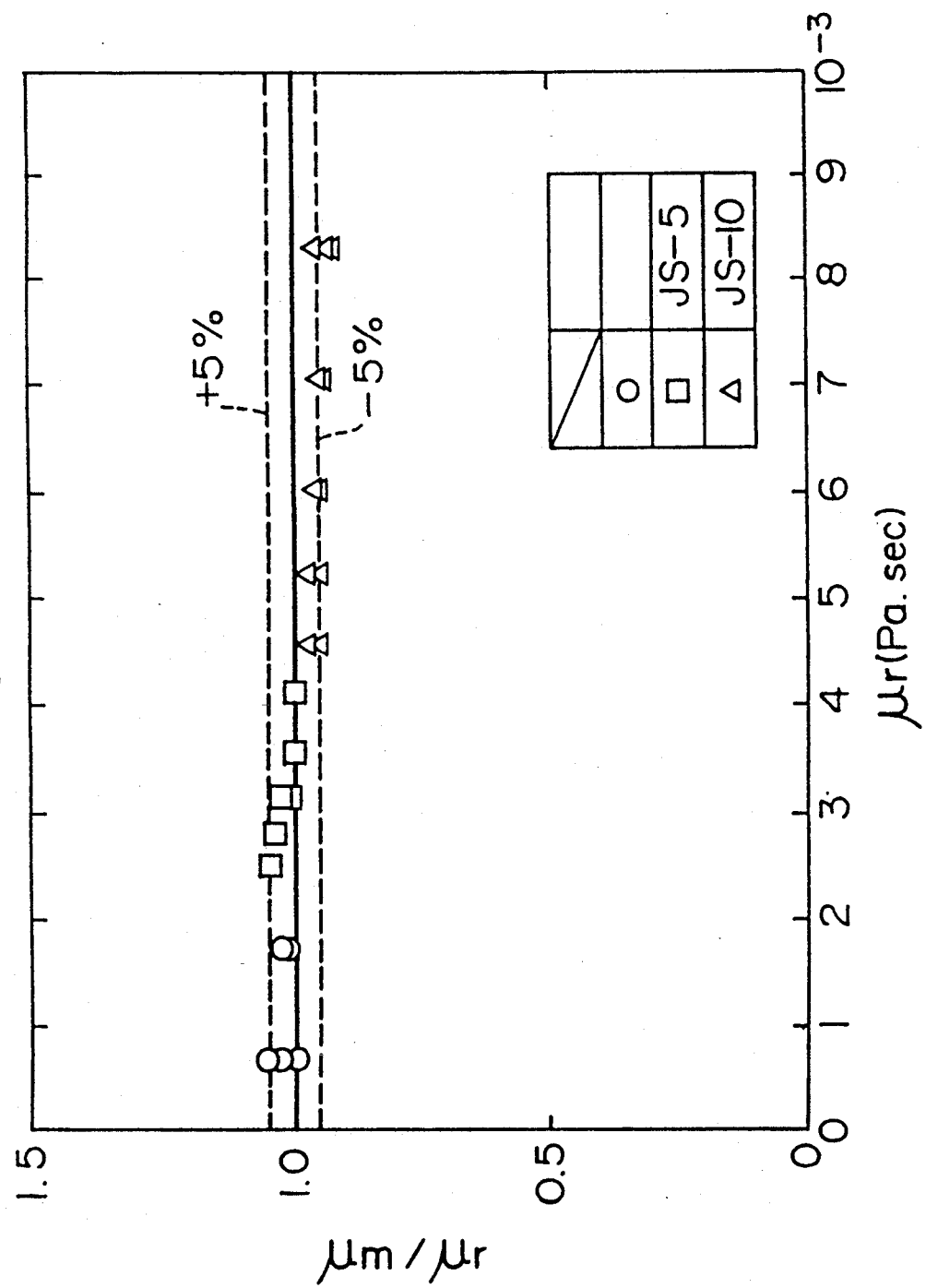
FIG. 6 is a graph showing the ratio of the measured viscosity and the true viscosity, obtained using water and viscosity standards for calibration of a viscometer.

The calibration of the device was made using water and viscosity standards defined in JIS Z8809 (JS 5 and JS 10 made by Japan Shell oil corporation). The water was filtered after distillation and ion-exchange. In the case of water, the calibration was carried out at the shear rate ranging from 50 to 10000/sec, while the shear rate for the viscosity standards were 3000 to 18000/sec. Results are shown in FIG. 6. In this Figure, the ratios of the viscosity measured, $\mu_m$, to the actual viscosity, $\mu_r$, are plotted as a function of the actual viscosity, $\mu_r$.

As can be seen from the results shown in FIG. 6, errors of measurements remain less than ±5% when the viscosity is less than $10^{-2}$ Pa.s, thus the viscometer of the present invention can be put into practical use without causing any problems. However, it is also possible to measure the liquid with the viscosity of more than $10^{-2}$ Pa.s, by suitable determination of the length of fine tube or piercing needle, capacity of the tubular vessel, the initial pressure (or vacuum) in the tubular vessel and the like. Causes for the errors may be a delay in response of the flow change to the change in pressure difference, and response detection of the pressure converter.

EXPERIMENT 3

The following discussion is provided under the assumption that the flow characteristics of the blood may be represented by a Newtonian model.

When charging out the measurements of the viscosity of human blood, the shear rate varies from 200 to 9000/sec. This range exceeds the range of shear rate being corrected, but no problem occurs as most of the data for use in determination of a flow curve are included in the range.

Figure 7:
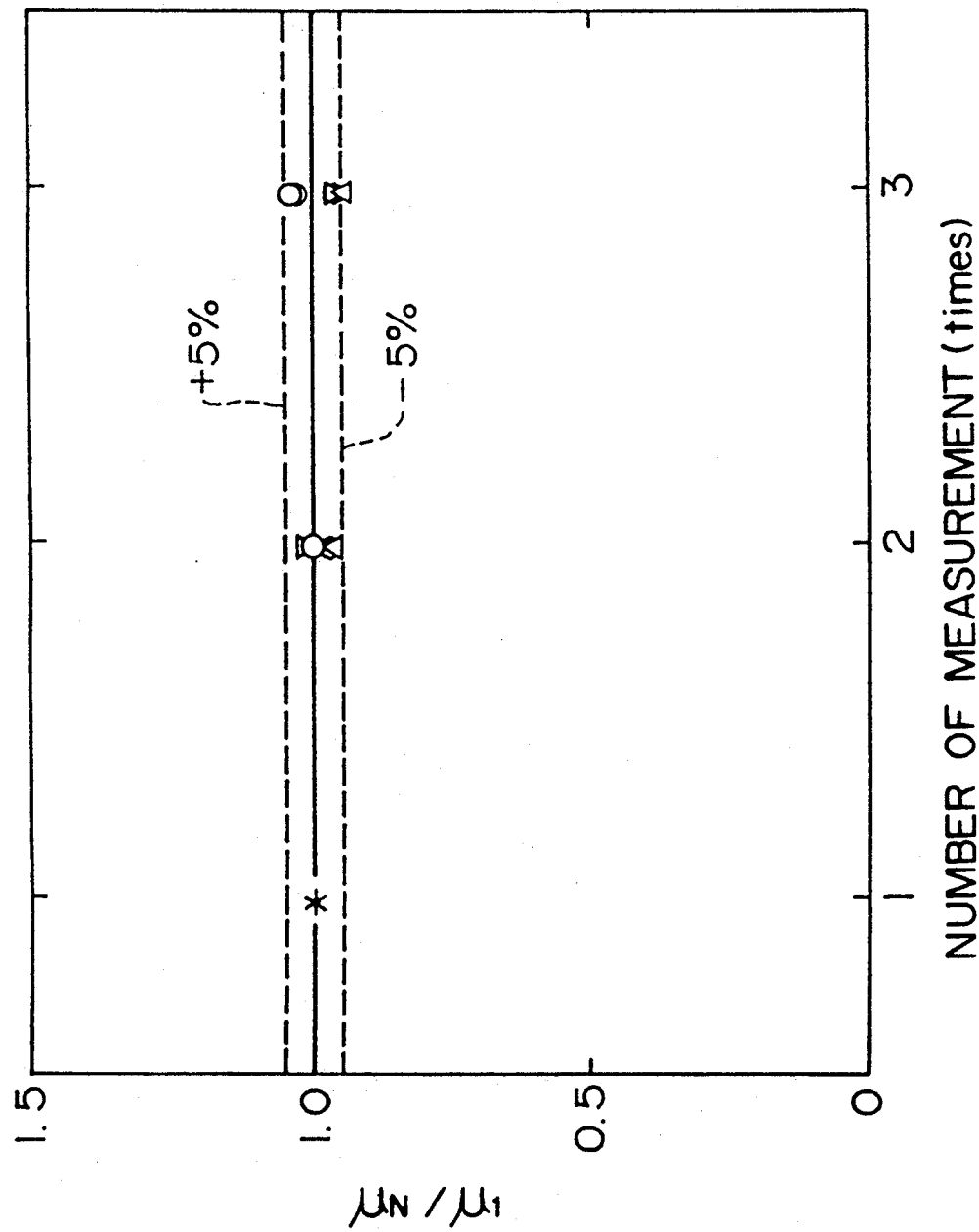
FIG. 7 is a graph showing the viscosity of the same blood measured by the device of FIG. 1.

In general, the blood causes hemolysis when placed under high shear rate. To observe effects of high shear rate on the human blood, the measurements were carried out with the same blood several times. That is, the blood subjected to the measurement of viscosity was poured into to the glass tube again, and then subjected to the measurement of viscosity. Results are shown in FIG. 7. A ratio of the $\mu_N/\mu_1$ is plotted as a function of the times of measurement, N.

From the results in FIG. 7, it can be understood that the viscometer of the present invention scarcely has effects on the blood even if measurements are carried out three times, as the ratio is in the range of 0.95 to 1.03. By measurement of hemolysis with the centrifuge, the hemolysis of the blood was slightly observed in only one of the five examples. It is believed that this results from the fact that the time required for passing through the fine tube is very short and ranges from 0.1 to 0.3 seconds. Further, it will be understood that the temperature change of the blood can be neglected as the time during which the blood passes through the fine tube is considerably short.

Figure 8:
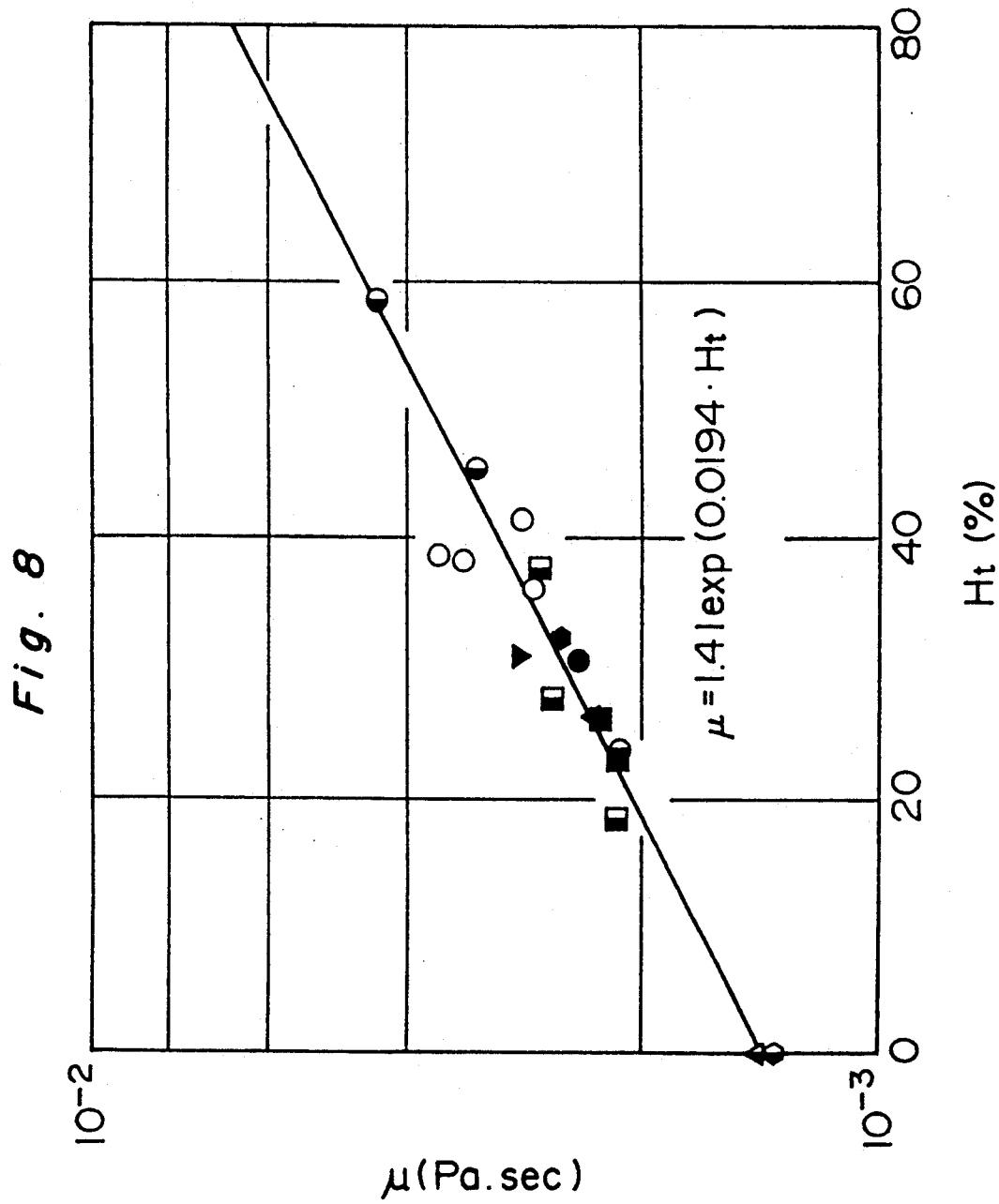
FIG. 8 is a graph showing the viscosity of bloods measured at various hematocrit values.

The bloods were directly drawn or collected from a person in normal health and anemic inpatients and subjected to measurements of viscosity. Separate from the above, the bloods collected from a person in normal health were centrifuged to separate red blood cell from the blood plasma, and the red cell was again mixed with the blood plasma in various ratios to prepare samples having various hematocrit values, i.e., a volume percentage of red blood cell to all the components of the blood. These blood samples were also subjected to the measurement of viscosity. Results are shown in FIG. 8. In this Figure, circles are data for the blood of normal persons, half black circles show the data for the samples with an adjusted hematocrit value, and black circles show data for the blood collected from anemic patients.

As can be seen from the data shown in FIG. 8, the values for the viscosity of the blood taken from the person in normal health are about $3.0 \times 10^{-3}$ Pa.s. This shows that the viscosity measurements made on the same samples in the prior viscometer and the viscometer of the present invention give equivalent values for the blood viscosity. Further, the viscosities of the blood collected from the anemic patients are about 2.4 Pa.s, which agree with the results obtained by using the viscometers of the prior art. It can be understood that the viscosity of the blood increases with the value of hematocrit. This agrees well with the results by the viscometers of the prior art. From the above results, the viscometer of the present invention makes it possible to measure the viscosity of human blood correctly and is applicable to clinical observations.

EXPERIMENT 4

Figure 9:
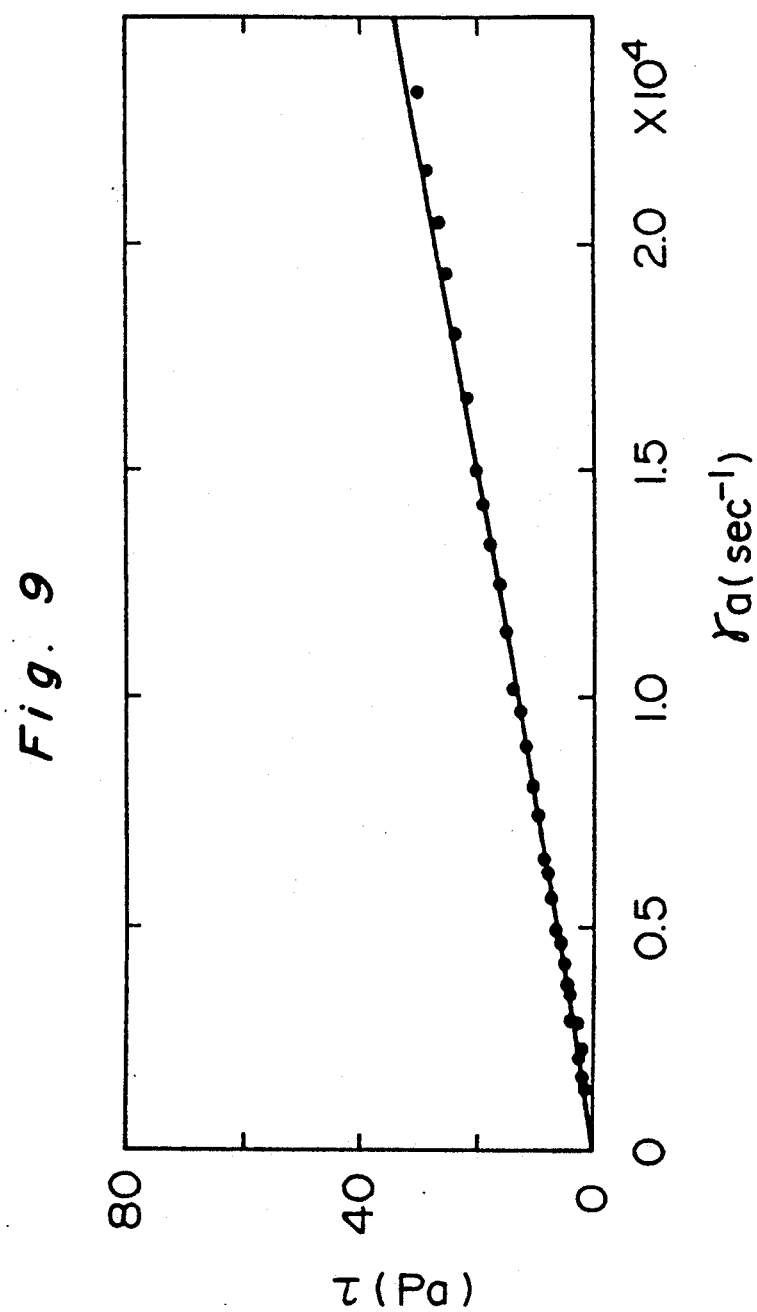
FIG. 9 is a graph showing the relationship between the shear stress and the shear rate of an emulsion of hexane and water.

There were prepared emulsions of an O/W type composed of water and hexane, which were then subjected to measurement of viscosity. The measurements were carried out at 20° C. in the same manner as example 1 with the viscometer having the construction shown in FIG. 1. Results are shown in FIG. 9 as a relationship between the shear rate and shear stress. The same results were reproduced by the experiments. The reproducibility was observed by several experiments.

From the results shown in FIG. 9, it will be seen that the emulsion is regarded as Newtonian. Further, it was observed that the viscosity of the emulsion increases with increase in the ratio of hexane to water.

EXPERIMENT 5

There were prepared aqueous solutions by dissolving polyacryl amide (PAA) in water, known as a viscoelastic fluid, to measure the viscosity with the viscometer of the present invention. The measurements were carried out at various temperatures in same manner as example 1. Results are shown in FIG. 10 as a relationship between the shear rate and shear stress. The same results were reproduced by several viscosity measurements made on the same samples.

From the results shown in FIG. 10, it can be seen that the aqueous solution of PAA behaves as an exponential fluid, i.e., as a non-Newtonian fluid. This shows that the viscometer of the present invention can be applied to measure the viscosity of non-Newtonian fluids.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A method for measurement of a viscosity of liquid, employing an evacuated hermetic tubular vessel with a predetermined reduced pressure and a fine tube of a uniform diameter bore, said method comprising the steps of:

(a) inserting one end of said fine tube into a first end of said tubular vessel, while dipping a second end of said fine tube opposite to said first end in a liquid to be measured, to cause the liquid to flow into said vessel through the fine tube under the influence of difference in pressure between said first and second ends of said fine tube;

(b) continuously detecting an internal pressure of said tubular vessel at predetermined intervals with a pressure sensor connected to said second end of the vessel to determine changes of the pressure difference between both ends of the fine tube with passage of time and changes of a flow rate of the liquid with passage of time; and (c) determining a viscosity of the liquid from the changes of pressure difference between said first and second ends of the fine tube and the changes of the flow rate of the liquid.

2. A method according to claim 1 wherein said fine tube is a hollow piercing needle.

3. The method according to claim 1, wherein said reduced pressure is 180 mmHg below atmospheric pressure.

4. The method according to claim 1, wherein said tubular vessel is maintained at a constant temperature.

5. The method according to claim 1, wherein said pressure difference between said first and second ends of the fine tube, $\Delta P_i$, and the flow rate of liquid, $Q_i$ are determined from the detected pressure by the following equations:

$$\Delta P_i = P_A - P_i + \pi g(h_i - H_i - L),$$

$$Q_i = (v_i - v_{i-1})/\Delta t, \text{ and}$$

$$P_0 V_0 = P_i v_i$$

where $P_0$ is an initial reduced pressure of the vessel at time $t_0$, $V_0$ is the initial volume of the vessel at time $t_0$, $P_i$ is a detected pressure at time $t_i$, $\rho$ is a density of the liquid, g is gravity acceleration, $P_A$ is the atmospheric pressure, $P_i$ is a pressure acting on the meniscus of the liquid in the vessel at time $t_i$, $h_i$ is a length of the fine tube being immersed in the liquid at time $t_i$, $H_i$ is a distance between said first end of the fine tube and the meniscus of the liquid in the vessel at time $t_i$, and L is a length of the fine tube, $v_i$ is a volume of the liquid in the vessel at time, $v_{i-1}$ is a volume at time $t_{i-1}$, and $\Delta t$ is an interval of measurement.

6. A device for measuring viscosity of liquids, comprising:

a tubular vessel sealed and maintained to a reduced pressure by a pair of rubber-like stoppers fitted within each opening of said vessel;

a hollow fine tube of uniform bore adapted to pierce one of said stoppers for entry into said vessel;

a pressure sensor connected to said vessel by a means for piercing a remaining one of the pair of stoppers to detect an internal pressure of said vessel;

an A/D converter electrically connected to said pressure sensor to convert its analogue signals to digital signals; and a computer for processing output signals of the A/D converter to determine a viscosity of the liquid from said output signals and the following equations:

$$\gamma(\tau_w) = -du/dr = 3\gamma_a/4 + (\tau_w/4)(d\gamma_a/d\tau_w)$$

$$\tau_w = \Delta PR/2L$$

$$\gamma_a = 4Q/\pi R^3$$

wherein $\Delta P$ is a pressure difference between both ends of the fine tube, R is a radius of the fine tube, L is a length of the fine tube, Q is a flow amount of the liquid per unit time, and a is the apparent shear rate (or apparent velocity gradient) at a point on the wall.

7. The device according to claim 6, wherein said fine tube is a hollow piercing needle.

8. The device according to claim 6, wherein said reduced pressure is 180 mmHg below atmospheric pressure.

9. The device according to claim 6, further comprising the step of maintaining said tubular vessel at a constant temperature.

* * * * *